United States Patent [19]

Junino et al.

[11] Patent Number: 5,226,924

[45] Date of Patent: Jul. 13, 1993

[54] 1,4-DI(MONO- OR POLY) HYDROXYALKYLAMINO-9,10-ANTHRAQUINONES FOR DYEING HUMAN KERATINOUS FIBRES, COSMETIC COMPOSITION CONTAINING THEM IN COMBINATION WITH AZO AND NITROBENZENE DYES, AND HAIR-DYEING PROCESS USING THEM

[75] Inventors: Alex Junino, Livry-Gargan; Alain Genet, Aulnay-sous-Bois, both of France

[73] Assignee: L'Oreal, Paris, France

[21] Appl. No.: 775,101

[22] Filed: Oct. 11, 1991

[30] Foreign Application Priority Data

Oct. 12, 1990 [FR] France ................. 90 12628

[51] Int. Cl.[5] ................................................. A61K 7/13
[52] U.S. Cl. ......................................... 8/405; 8/406; 8/425; 8/428; 8/429; 8/435; 424/70
[58] Field of Search ............. 8/405, 406, 425, 428, 8/429, 435; 424/70

[56] References Cited

U.S. PATENT DOCUMENTS

| | | | |
|---|---|---|---|
| 2,199,813 | 5/1940 | Baumann et al. | 552/247 |
| 3,806,525 | 4/1974 | Kalopissis et al. | 260/380 |
| 3,811,830 | 5/1974 | DeMarco | 8/425 |
| 4,268,264 | 5/1981 | Grollier et al. | 8/410 |
| 4,295,848 | 10/1981 | Grollier et al. | 8/410 |
| 4,391,603 | 7/1983 | Rosenbaum et al. | 8/405 |
| 4,425,132 | 1/1984 | Grollier et al. | 8/405 |
| 4,602,913 | 7/1986 | Grollier et al. | 8/405 |
| 4,867,751 | 9/1989 | Lang et al. | 8/405 |
| 4,886,517 | 12/1989 | Bugart et al. | 8/405 |
| 5,112,359 | 5/1992 | Murphy et al. | 8/405 |

FOREIGN PATENT DOCUMENTS

| | | |
|---|---|---|
| 1469797 | 12/1968 | Fed. Rep. of Germany. |
| 489697 | 12/1936 | United Kingdom. |
| 2093867 | 9/1982 | United Kingdom. |

OTHER PUBLICATIONS

French Search Report of FR 90 12628.

*Primary Examiner*—Paul Lieberman
*Assistant Examiner*—William S. Parks
*Attorney, Agent, or Firm*—Cushman, Darby & Cushman

[57] ABSTRACT

The present invention relates to the use of 1,4-di(mono- or poly)hydroxyalkylamino-9,10-anthraquinones:

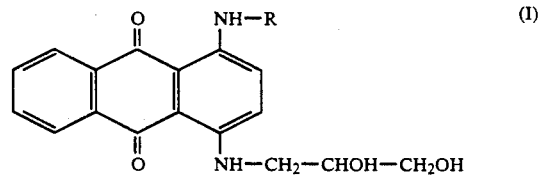

where R represents a $C_2$ to $C_6$ monohydroxyalkyl radical or a $C_3$ to $C_6$ polyhydroxyalkyl radical for dyeing human keratinous fibers, to the dyeing cosmetic compositions containing such anthraquinones, to the dyeing compositions for keratinous fibers containing such anthraquinones in combination with nitro dyes of the benzene type and azo dyes for direct dyeing, and/or with oxidation dyes for oxidation dyeing as well as to the processes for dyeing keratinous fibers by direct dyeing or by oxidation dyeing.

16 Claims, No Drawings

1,4-DI(MONO- OR POLY) HYDROXYALKYLAMINO-9,10-ANTHRAQUINONES FOR DYEING HUMAN KERATINOUS FIBRES, COSMETIC COMPOSITION CONTAINING THEM IN COMBINATION WITH AZO AND NITROBENZENE DYES, AND HAIR-DYEING PROCESS USING THEM

The present invention relates to the use of 1,4-di(mono- or poly)hydroxyalkylamino-9,10-anthraquinones for dyeing human keratinous fibers, the dyeing cosmetic compositions containing such anthraquinones and the keratinous fibers dyeing compositions containing such anthraquinones in combination with nitro dyes of the benzene type and azo dyes for direct dyeing, and/or with oxidation dyes for oxidation dyeing, as well as the processes for dyeing keratinous fibers by direct dyeing or by oxidation dyeing.

The use is known of either oxidation dyes or of direct dyes as dyes for dyeing human keratinous fibers.

The oxidation dyes lead to masking and durable shades, but their high durability and their very high affinity for hair, often involves the appearance of the phenomenon known in the art of dyeing, namely the phenomenon of demarcation between the tips and the half-lengths dyed on the one hand, and the roots not dyed on the other hand.

In the case of direct dyes and in particular of nitro dyes of the benzene type, this defect does not appear and, accordingly, the nitro dyes of the benzene type are often used in the field of direct dyeing. Nevertheless, these direct dyes exhibit the disadvantage, in some cases, of having an insufficient affinity for nonsensitized natural hair.

In order to palliate this defect, an attempt has been made to combine some dyes and in particular cosmetic dyes of the azo or aminoanthraquinone type with nitro dyes of the benzene type.

In the class of aminoanthraquinone dyes, 1,4,5,8-tetraaminoanthraquinone (Colour Index 64500) which exhibits the disadvantage of being very sparingly soluble in organic solvents or in water/solvent media constituting the basis of hair dyeing products is described in particular.

The applicant have now demonstrated, surprisingly, that some di(mono- or poly)hydroxyalkylamino-9,10-anthraquinones exhibit not only the advantage of an excellent solubility in the usual solvent media and dye carriers, but also that of giving durable dyes which are stable, in particular to washes, light, atmospheric aggressions, chemical agents, perspiration, and finally that of a satisfactory innocuousness which makes their use possible in dyeing human keratinous fibers.

Accordingly, the present invention relates to the use, for dyeing human keratinous fibers, of anthraquinones of formula:

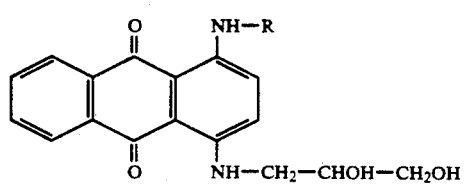

where R represents a $C_2$ to $C_6$ monohydroxyalkyl radical or a $C_3$ to $C_6$ polyhydroxyalkyl radical, for dyeing human keratinous fibres.

In formula (I), $C_3$ to $C_6$ alkyl is understood as meaning the linear or branched alkyl radicals comprising 3 to 6 carbon atoms. The dihydroxyalkyls are preferred among the polyhydroxyalkyls.

These anthraquinones of formula (I) are known by Patent US-A-2,199,813. This patent, however, describes these compounds only as dyes for synthetic fibers.

The invention therefore relates, in particular, to the use of 1,4-di($\beta$,$\gamma$-dihydroxypropylanino)-9,10-anthraquinone (formula (I) where R represents $CH_2$—$CHOH$—$CH_2OH$) and of 1-($\beta$-hydroxyethylamino)-4-($\beta$,$\gamma$-dihydroxypropylamino)-9,10-anthraquinone (formula (I) where R represents $CH_2$—$CH_2OH$) for dyeing human keratinous fibers.

Another subject of the invention consists of the cosmetic compositions comprising one or more anthraquinones of formula:

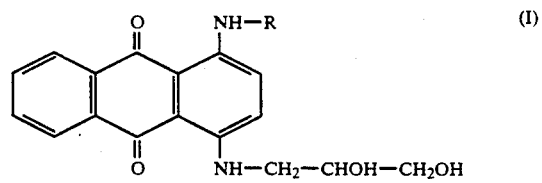

and, in addition, at least one of the cosmetic adjuvants chosen from anionic, cationic, nonionic, amphoteric surface-active agents or their mixtures, thickeners, dispersing agents, penetrating agents, sequestrants, film-forming agents, hair treating agents, buffers, perfumes, alkalinizing or acidifying agents, opacifying agents or preservatives.

Among these cosmetic compositions, those which contain the anthraquinones of formula (I) where R represents $CH_2$—$CHOH$—$CH_2OH$ or $CH_2$—$CH_2OH$ are preferred.

Another subject of the invention consists of the keratinous fiber dyeing compositions, characterised in that they comprise one or more anthraquinones of formula (I):

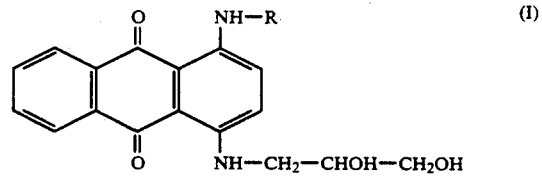

where R has the meaning indicated above, in combination with one or more other dyes chosen from:
(i) nitro dyes of the benzene type;
(ii) dyes of the azo type;
(iii) oxidation dye precursors.

According to a first embodiment of the invention, the anthraquinone dye or dyes of formula (I) is/are used in combination with at least one nitro dye of the benzene type.

Among the nitro dyes of the benzene type, the blue or violet nitrobenzene dyes belonging to the class of nitroparaphenylenediamines, having a shade or "hue" according to Munsell of between 2.5 B and 10 RP, according to the publication in *Officiel Digest*, April 1975, page 375, FIG. 2, are preferred.

However, other yellow, orange or red nitrobenzene dyes giving shades which are not between 2.5 B and 10 RP, belonging to the nitrophenylenediamine series or to other nitrobenzene dye series and in particular for example nitroaminophenols, nitroaminoalkoxybenzenes or nitroaminohydroxyalkoxybenzenes, may be also used in combination with the aminoanthraquinone or aminoanthraquinones of formula (I).

Among the preferred blue or violet nitro dyes of the benzene type belonging to the class of nitroparaphenylenediamines, there may be mentioned:

2-N-methylamino-5-[N,N-bis(β-hydroxyethyl)amino]-nitrobenzene;

2-N-methylamino-5-[N-methyl-N-(β-hydroxyethyl)amino]-nitrobenzene;

2-(N-β-hydroxyethyl)amino-5-[N,N-bis(β-hydroxyethyl)amino]nitrobenzene;

2-(N-β-hydroxyethyl)amino-5-[N-methyl-N-(β-hydroxyethyl)amono]nitrobenzene;

2-(N-γ-hydroxypropyl)amino-5-[N,N-bis(β-hydroxyethyl)amino]nitrobenzene;

2-(N-β-aminoethyl)amino-5-[N,N-bis(β-hydroxyethyl)amino]nitrobenzene;

2-N-methylamino-5-[N-methyl-N-(β,γ-dihydroxypropyl)amino]nitrobenzene;

2-amino-5-[N,N-bis(β-hydroxyethyl)amino]nitrobenzene;

2-N-(β-hydroxyethyl)amino-5-]N-(β-hydroxyethyl)amino]nitrobenzene;

2-N-(β-hydroxyethyl-amino-5-]N-ethyl)N-(β-hydroxyethyl)amino]nitrobenzene.

Among the nitrobenzene dyes whose shades are not between 2.5 B and 10 RP, there may be mentioned in particular:

2-amino-5-N-methylaminonitrobenzene,
2,4-diaminonitrobenzene,
3,4-diaminonitrobenzene,
2,5-diaminonitrobenzene,
3-amino-4-hydroxynitrobenzene,
3-hydroxy-4-aminonitrobenzene,
2-hydroxy-5-aminonitrobenzene,
2-amino-5-hydroxynitrobenzene,
2-amino-3-hydroxynitrobenzene,
2-amino-5-N-(β-hydroxyethyl)aminonitrobenzene,
2-N-(β-hydroxyethyl)amino-5-hydroxynitrobenzene,
3-methoxy-4-N-(β-hydroxyethyl)aminonitrobenzene,
2-N-methylamino-4-(β-hydroxyethyloxy)nitrobenzene,
2-amino-3-methylnitrobenzene,
2-N-(β-hydroxyethyl)amino-5-aminonitrobenzene,
2-amino-4-chloro-5-N-(β-hydroxyethyl)aminonitrobenzene,
2-amino-4-methyl-5-N-(β-hydroxyethyl)aminonitrobenzene,
2-amino-4-methyl-5-N-methylaminonitrobenzene,
2-N-(β-hydroxyethyl)amino-5-methoxynitrobenzene,
2-amino-5-(β-hydroxyethyloxy)nitrobenzene,
2-N-(β-hydroxyethyl)aminonitrobenzene,
3-amino-4-N-(β-hydroxyethyl)aminonitrobenzene,
3-(β-hydroxyethyloxy)-4-N-(β-hydroxyethyl)aminonitrobenzene,
2-N-methylamino-4-(β,γ-dihydroxypropyloxy)nitrobenzene,
2-N-(β-hydroxyethyl)amino-5-(β-hydroxyethyloxy)nitrobenzene,
2-N-(β-hydroxyethyl)amino-5-(β,α-dihydroxypropyloxy)nitrobenzene,
3-hydroxy-4-N-(β-hydroxyethyl)aminonitrobenzene,
3-N-(β-hydroxyethyl)amino-4-N-(β-hydroxyethyl)aminonitrobenzene,
2-amino-4-methyl-5-N-(β,γ-dihydroxypropyl)aminonitrobenzene,
2-amino-4-methyl-5-hydroxynitrobenzene,
2-N-(β-aminoethyl)amino-4-methoxynitrobenzene,
2-N-(β-aminoethyl)aminonitrobenzene,
2-N-(β-aminoethyl)amino-5-N-(β-hydroxyethyl)aminonitrobenzene,
2-amino-4-methyl-5-N-(β-aminoethyl)aminonitrobenzene,
2-amino-4-chloro-5-N-(β-aminoethyl)aminonitrobenzene,
2-N-(β-hydroxypropyl)amino-5-hydroxynitrobenzene,
2,6-diaminonitrobenzene,
2-N-(β-hydroxyethyl)amino-6-aminonitrobenzene,
2,6-di(β-hydroxyethylamino)nitrobenzene,
2-N-ethylamino-5-carboxynitrobenzene,
2-nitro-4-aminodiphenylamine-2'-carboxylic acid,
3-N-ethylamino-4-hydroxy-5-chloronitrobenzene,
2-N-(β-hydroxyethyl)amino-5-methoxy-2,3-dinitrobenzene,
2-N-(β,γ-dihydroxypropyl)amino-5-methoxy-2,3-dinitrobenzene,
2-N-(β-hydroxyethyl)amino-5-trifluoromethylnitrobenzene,
2-N-(β,γ-dihydroxypropyl)amino-5-trifluoromethylnitrobenzene,
2-N-(β-hydroxyethyl)amino-5-methylnitrobenzene.

According to a second embodiment, the anthraquinone dye or dyes of formula (I) is/are used according to the invention in combination with at least one dye of the azo type.

Among the azo dyes, there may be mentioned:
1-(4'-aminophenylazo)-4-nitrobenzene,
1-(4'-nitrophenylazo)-2-methyl-4-di(β-hydroxyethyl)aminobenzene,
1-(4'-aminodiphenylazo)-2-methyl-4-di(β-hydroxyethyl)aminobenzene,
1-[4'-di(β-hydroxyethyl)aminophenylazo]-4-aminobenzene, or
4-amino-2'-methyl-4'-N,N-di(β-hydroxyethyl)aminophenylazobenzene.

In the compositions according to the invention the anthraquinone dye or dyes of formula (I) are present in proportions ranging from 0.01 to 5% by weight of the total weight of the composition.

In the case where the anthraquinones according to the invention are combined with nitro dyes of the benzene type, the latter are present in proportions ranging from 0.01 to 10% of the total weight of the dyeing composition.

In the case where the anthraquinones according to the invention are combined with azo dyes, the latter are present in proportions ranging from 0.005 to 5% of the total weight of the dyeing composition.

According to a third embodiment, and which is preferred according to the invention, the anthraquinone dye or dyes of formula (I) according to the invention are used in combination with at least one nitro dye of the benzene type described above and with at least one azo dye described above. The nitrobenzene, azo or anthraquinone dyes according to the invention are then present in the compositions in the concentrations described above.

In another embodiment of the invention, the aminoanthraquinone compounds of formula (I) according to the invention are used in combination with oxidation dye precursors and optionally with other direct dyes. These oxidation dye precursors are preferably chosen from paraphenylenediamines, para-aminophenols, heterocyclic bases such as for example 2,5-diaminopyridine or 7-aminobenzomorpholine or ortho-aminophenols.

Moreover, these compositions may contain, in combination with the oxidation dye precursors above, couplers known in the state of the art. By way of couplers, meta-diphenols, meta-aminophenols, meta-phenylenediamines, meta-acylaminophenols, meta-ureidophenols, meta-carbalkoxyaminophenols, α-naphthol, as well as couplers possessing an active methylene group such as diketonic compounds, as well as heterocylic couplers, may be mentioned in particular.

In this embodiment of the invention, the oxidation dye precursors are used at concentrations between 0.01 and 10% by weight, preferably between 0.03 and 5% by weight, based on the total weight of the composition. For their part, the couplers may be present in these compositions in proportions ranging from 0.001 to 8% by weight, and preferably between 0.015 and 5% by weight.

In this embodiment where oxidation dye precursors are present, the compositions may, in addition, contain reducing or antioxidizing agents, which are in this case present in proportions of between 0.05 and 3% by weight relative to the total weight of the composition.

When the dyeing compositions according to the invention constitute oxidation dyes, that is to say comprising oxidation dye precursors, and therefore involve developing by an oxidant, the anthraquinone dye according to the invention is essentially used in order to confer glints to the final dyeing.

The compositions according to the invention may in addition also contain other aminoanthraquinone dyes and in particular 1,4-(di-β-hydroxyethylamino)-9,10-anthraquinone and nitropyridine dyes.

The compositions according to the invention may comprise as a suitable carrier for their application, water and/or cosmetically acceptable organic solvents, and, more particularly alcohols such as ethyl alcohol, isopropyl alcohol, benzyl alcohol and phenylethyl alcohol, or glycols or glycol ethers such as for example ethylene glycol and its monomethyl, monoethyl and monobutyl ethers, propylene glycol, butylene glycol, dipropylene glycol, as well as alkyl ethers of diethylene glycol, such as for example monomethyl ether or monobutyl ether of diethylene glycol. The concentration of these organic solvents is in this case for example between 0.5 and 20%, and preferably 2 and 10% by weight relative to the total weight of the composition.

Fatty amides such as mono- and diethanolamides of acids derived from copra, lauric acid or oleic acid, may also be added to the composition according to the invention at concentrations of between 0.05 and 10% by weight.

Anionic, cationic, nonionic or amphoteric surface-active agents or their mixtures may also be added to the composition according to the invention. Preferably, the surface-active agents are present in the composition according to the invention in a proportion of between 0.1 and 50% by weight, and preferably between 1 and 20% by weight relative to the total weight of the composition.

As thickening products which may be optionally added to the composition according to the invention, sodium alginate, gum arabic, guar gum, xanthan gums and cellulose derivatives as well as acrylic acid polymers may be mentioned in particular.

Inorganic thickening agents such as bentonite may also be used. These thickeners are used alone or in a mixture, and are preferably present in a proportion of between 0.5 and 5% by weight relative to the total weight of the composition, and advantageously, between 0.5 and 3% by weight.

The compositions according to the invention may be formulated at acidic, neutral or alkaline pH, it being possible for the pH to vary between 4 and 10.5, and preferably between 6 and 10.

Among the alkalinizing agents which may be used, alkanolamines, alkaline hydroxides and carbonates or ammonium hydroxide may be mentioned.

Among the acidifying agents which may be used, lactic acid, acetic acid, tartaric acid, phosphoric acid, hydrochloric acid and citric acid may be mentioned.

The dyeing compositions may in addition contain various customary adjuvants such as perfumes, sequestering agents, film-forming products and hair treating agents, dispersing agents, hair conditioning agents, preserving agents, opacifiers, as well as any other adjuvant normally used in cosmetics.

The compositions according to the invention may be provided in various customary forms for the treatment of keratinous fibers, such as thickened or gelled liquids, creams or foams or in any other suitable forms for achieving such dyeing.

The present invention furthermore relates to a process for dyeing human keratinous fibers in which a composition according to the invention is applied to keratinous fibers for direct dyeing.

It furthermore relates to a process for oxidation dyeing, in which there is applied a composition according to the invention comprising at least one oxidation dye precursor and, simultaneously or thereafter, an oxidizing agent.

Thus, if the dyeing composition contains oxidation dyes, it may be mixed at the time of use with an oxidising agent. This oxidizing agent is normally hydrogen peroxide titrating 10 to 40 volumes. The application may thus be simultaneous or, alternatively, sequential, that is to say that the composition containing the oxidizing agent is applied after the dyeing composition containing the oxidation dyes.

In the case where the composition according to the invention contains oxidation dyes, the composition or the compositions are applied to hair for 1 to 60 minutes, and preferably 10 to 45 minutes, and then rinsed.

In the case where the dyeing composition contains only direct dyes, it is applied to hair for an exposure time varying between 1 and 60 minutes, and preferably 5 and 45 minutes and then rinsed.

In each of the two cases above, the hair may optionally be washed, rinsed again and dried.

The dyeing compositions conforming to the invention may be applied to natural or dyed hair, permanent-waved or not, or to hair which is highly or lightly bleached and, optionally, permanently waved.

The present invention furthermore relates to dyeing kits or multicomponent devices comprising at least one compartment containing the composition according to the invention where oxidation dyes are present, and the other comprising the oxidizing agent.

Other advantages and characteristics of the invention will emerge from the examples below, which are given by way of illustration with no limitation being implied.

EXAMPLE 1

| | |
|---|---|
| 1,4-di(β,γ-dihydroxypropylamino)-9,10-anthraquinone | 0.25 g |
| 2-butoxyethanol | 10.0 g |
| hydroxyethyl cellulose ("Cellosize WPO 3H" from the company UNION CARBIDE) | 2.0 g |
| Sodium lauryl ether sulphate containing 2 moles of ethylene oxide ("Sactipon 8533" from the company LEVER) | 3.0 g AS |
| 2-amino-2-methyl-1-propanol | qs pH = 9.5 |
| deionized water | qs 100.0 g |

This composition when applied for an exposure time of 30 minutes to natural grey hair which is 90% white, confers to it a blue shade after rinsing and drying.

EXAMPLE 2

| | |
|---|---|
| 1,4-di(β,γ-dihydroxypropylamino)-9,10-anthraquinone | 0.2 g |
| 4-amino-2'-methyl-4'-N,N-di-(β-hydroxyethyl)aminophenylazobenzene | 0.1 g |
| 2-ethoxyethanol | 10.0 g |
| nonylphenol containing 9 moles of ethylene oxide ("Simulsol 830 NP" from the company SEPPIC) | 2.0 g |
| triethanolamine | qs pH = 6.5 |
| deionized water | qs 100.0 g |

This composition is applied to natural grey hair which is 90% white and left in contact for 20 minutes. After rinsing and drying, a green color is obtained.

EXAMPLE 3

| | |
|---|---|
| 1,4-di(β,γ-dihydroxypropylamino)-9,10 -anthraquinone | 0.5 g |
| 4-amino-2'-methyl-4'-N,N-di-(β-hydroxyethyl)aminophenylazobenzene | 0.1 g |
| 2-N-(β-hydroxyethyl)amino-5-N,N-di-(β-hydroxyethyl)aminonitrobenzene | 1.0 g |
| 2-N-methylamino-5-N-methyl-N-β,γ-di-(hydroxypropyl)aminonitrobenzene | 0.5 g |
| 2-N-methylamino-4-β,γ-dihyroxypropyl-oxynitrobenzene | 0.5 g |
| 2-N-methylamino-4-(β-hydroxyethyl)amino-nitrobenzene | 0.1 g |
| oleyl diethanolamide | 3.0 g |
| lauric acid | 1.0 g |
| 2-ethoxyethanol | 5.0 g |
| "Cellosive WPO 3H" (UNION CARBIDE) | 2.0 g |
| 2-amino-2-methyl-1-propanol | qs pH = 9.5 |
| deionized water | qs 100.0 g |

This composition is applied to grey permanent-waved hair which is 90% white and left in contact for 20 minutes. After rinsing and drying, the hair has a dark chestnut shade.

EXAMPLE 4

| | |
|---|---|
| 1,4-di(β,γ-dihydroxypropylamino-9,10-anthraquinone | 0.3 g |
| 2-methyl-1,4-diaminobenzene | 0.8 g |
| p-aminophenol | 0.05 g |
| 1-methyl-2-hydroxy-4-β-hydroxyethyl-aminobenzene | 0.95 g |
| m-aminophenol | 0.3 g |
| xanthan gum, sold by the company KELCO under the name "KELTROL T" | 2.2 g |
| sodium alkyl ether sulphate containing 28% of AS, sold under the name "SACTIPON 8533" by the company LEVER | 20.0 g |
| oleyl diethanolamide | 2.5 g |
| ethylenediaminotetraacetic acid | 0.1 g |
| thiolactic acid | 0.3 g |
| ammonium hydroxide containing 20% of NH₃ | 12.0 g |
| water | qs 100.0 g |

This gelled composition is diluted at the time of use with an equal weight of $H_2O_2$ at 20 volumes. The mixture obtained is applied to natural brown hair and left in contact for 30 minutes.

A violine chestnut shade is obtained after rinsing, shampooing and drying.

We claim:

1. A composition for dyeing keratinous fibers comprising in a cosmetically acceptable carrier suitable for dyeing said fibers at least one anthraquinone having the formula

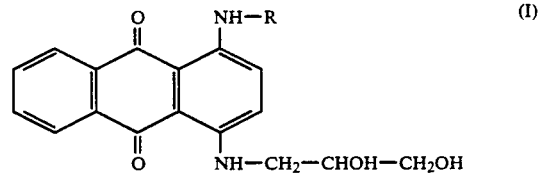

wherein R represents a $C_2$–$C_6$ monohydroxyalkyl radical or a $C_3$–$C_6$ polyhydroxyalkyl radical, said anthraquinone being present in an amount ranging from 0.01 to 5 percent by weight based on the total weight of said composition and being combined with at least one dye component selected from the group consisting essentially of (i) a nitro dye of the benzene series present in an amount ranging from 0.01 to 10 percent by weight based on the total weight of said composition, (ii) an azo dye present in an amount ranging from 0.005 to 5 percent by weight based on the total weight of said composition and (iii) an oxidation dye precursor present in an amount ranging form 0.001 to 8 percent by weight based on the total weight of said composition.

2. The composition of claim 1 where in said anthraquinone of formula (I) R represents $CH_2$—CHOH—$CH_2OH$ or $CH_2$—$CH_2OH$.

3. The composition of claim 1 wherein said nitro dye of the benzene series is a blue or violet nitroparaphenylenediamine dye having a shade, according to Munsell, of between 2.5B and 10RP.

4. The composition of claim 3 wherein said nitro dye of the benzene series is selected from the group consisting of
2-N-methylamino-5-[N,N-bis(β-hydroxyethyl)amino] nitrobenzene,
2-N-methylamino-5-[N-methyl-N-(β-hydroxyethyl)amino] nitrobenzene,
2-(N-β-hydroxyethyl)amino-5-[N,N-bis(β-hydroxyethyl)amino] nitrobenzene,
2-(N-β-hydroxyethyl)amino-5-[N-methyl-N-(β-hydroxyethyl)amino] nitrobenzene,
2-(N-γ-hydroxypropyl)amino-5-[N,N-bis(β-hydroxyethyl)amino] benzene,
2-(N-β-aminoethyl)amino-5-[N,N-bis(β-hydroxyethyl)amino] nitrobenzene,
2-N-methylamino-5-[N-methyl-N-(β,γ-dihydroxypropyl)amino] nitrobenzene, 2-amino-5-[N,N-bis(β-hydroxyethyl)amino] nitrobenzene,
2-N-(β-hydroxyethyl)amino-5-[N-(β-hydroxyethyl)amino] nitrobenzene and
2-N-(β-hydroxyethyl)amino-5-[N-ethyl-N-(β-hydroxyethyl)amino] nitrobenzene.

5. The composition of claim 1 wherein said nitro dye of the benzene series is selected from the group consisting of a yellow nitrophenylenediamine, an orange nitrophenylenediamine, a red nitrophenylenediamine, a nitroaminophenol, a nitroaminoalkoxybenzene, and a nitroaminohydroxyalkoxybenzene.

6. The composition of claim 5 wherein said nitro dye of the benzene series is selected from the group consisting of
2-amino-5-N-methylaminonitrobenzene,
2,4-diaminonitrobenzene,
3,4-diaminonitrobenzene,
2,5-diaminonitrobenzene,
3-amino-4-hydroxynitrobenzene,
3-hydroxy-4-aminonitrobenzene,
2-hydroxy-5-aminonitrobenzene,
2-amino-5-hydroxynitrobenzene,
2-amino-3-hydroxynitrobenzene,
2-amino-5-N-(β-hydroxyethyl) aminonitrobenzene,
2-N-(β-hydroxyethyl) amino-5-hydroxynitrobenzene,
3-methoxy-4-N-(β-hydroxyethyl) aminonitrobenzene,
2-N-methylamino-4-(β-hydroxyethyloxy) nitorbenzene,
2-amino-3-methylnitrobenzene,
2-N-(β-hydroxyethyl) amino-5-aminonitrobenzene,
2-amino-4-chloro-5-N-(β-hydroxyethyl) aminonitrobenzene,
2-amino-4-methyl-5-N-(β-hydroxyethyl) aminonitrobenzene,
2-amino-4-methyl-5-N-methylaminonitrobenzene,
2-N-(β-hydroxyethyl)amino-5-methoxynitrobenzene,
2-amino-5-(β-hydroxyethyloxy) nitrobenzene,
2-N-(β-hydroxyethyl) aminonitrobenzene,
3-amino-4-N-(β-hydroxyethyl) aminonitrobenzene,
3-(β-hydroxyethyloxy)-4-N-(β-hydroxyethyl) aminonitrobenzene,
2-N-methylamino-4-(β,γ-dihydroxypropyloxy) nitrobenzene,
2-N-(β-hydroxyethyl)amino-5-(β-hydroxyethyloxy) nitrobenzene,
2-N-(β-hydroxyethyl)amino-5-(β,α-dihydroxypropyloxy) nitrobenzene,
3-hydroxy-4-N-(β-hydroxyethyl) aminonitrobenzene,
3-N-(β-hydroxyethyl)amino-4-N-(β-hydroxyethyl) aminonitrobenzene,
2-amino-4-methyl-5-N-(β,γ-dihydroxypropyl) aminonitrobenzene,
2-amino-4-methyl-5-hydroxynitrobenzene,
2-N-(β-aminoethyl)amino-4-methoxynitrobenzene,
2-N-(β-aminoethyl) aminonitrobenzene,
2-N-(β-aminoethyl) amino-5-N-(β-hydroxyethyl) aminonitrobenzene,
2-amino-4-methyl-5-N-(β-aminoethyl) aminonitrobenzene,
2-amino-4-chloro-5-N-(β-aminoethyl) aminonitrobenzene,
2-N-(β-hydroxypropyl)amino-5-hydroxynitrobenzene,
2,6-diaminonitrobenzene,
2-N-(β-hydroxyethyl) amino-6-aminonitrobenzene,
2,6-di(β-hydroxyethylamino) nitrobenzene,
2-N-ethylamino-5-carboxynitrobenzene,
2-nitro-4-aminodiphenylamine-2'-carboxylic acid,
3-N-ethylamino-4-hydroxy-5-chloronitrobenzene,
2-N-(β-hydroxyethyl)amino-5-methoxy-2,3-dinitrobenzene,
2-N-(β,γ-hydroxyethyl)amino-5-methoxy-2,3-dinitrobenzene,
2-N-(β-hydroxyethyl)amino-5-trifluoromethylnitrobenzene,
2-N-(β-γ-dihydroxypropyl)amino-5-trifluoromethylnitrobenzene and
2-N-(β-hydroxyethyl)amino-5-methylnitrobenzene.

7. The composition of claim 1 which also includes a nitro dye of the nitropyridine type or an anthraquinone compound other than the anthraquinone of formula (I).

8. The composition of claim 1 wherein said azo dye is selected from the group consisting of
1-(4'-aminophenylazo)-4-nitrobenzene,
1-(4'-nitrophenylazo)-2-methyl-4-di(β-hydroxyethyl) aminobenzene,
1-(4'-aminodiphenylazo)-2-methyl-4-di(β-hydroxyethyl) aminobenzene,
1-[4'-di(β-hydroxyethyl) aminophenylazo]-4-aminobenzene, and
4-amino-2'-methyl-4'-N,N-di(β-hydroxyethyl) aminophenylazobenzene.

9. The composition of claim 1 wherein said oxidation dye precursor is selected from the group consisting of a paraphenylenediamine, a para-aminophenol, a heterocyclic base and an ortho-aminophenol.

10. The composition of claim 9 which also contains a coupler selected from the group consisting of a meta-diphenol, a meta-aminophenol, a meta-phenylenediamine, a meta-acylaminophenol, a meta-ureidophenol, a meta-carbalkoxyaminophenol, an α-naphthol, a diketonic compound and a heterocyclic coupler, said coupler being present in an amount ranging from 0.001 to 8 percent by weight.

11. The composition of claim 10 wherein said coupler is present in an amount ranging from 0.015 to 5 percent by weight.

12. The composition of claim 1 which also includes a reducing agent or an anti-oxidizing agent, present in an amount ranging from 0.05 to 3 percent by weight based on the total weight of said composition.

13. The composition of claim 1 which also includes a cosmetic adjuvant selected from the group consisting of an anionic, cationic, nonionic or amphoteric surfactant or a mixture thereof; a thickener; a dispersing agent; a penetrating agent; a sequesterant; a film-forming agent; a buffer; a perfume; an alkalinizing agent; an acidifying agent; a pearling agent and a solubilizing agent.

14. A process for direct dyeing of keratinous fibers comprising applying to said fibers the composition of claim 1.

15. A process for the oxidation dye of keratinous fibers comprising applying to said fibers the composition of claim 1, said composition containing an exidation dye precursor, and simultaneously or subsequently applying to said fibers an oxidizing agent present in a cosmetically acceptable medium.

16. A multi-compartment kit for use in dyeing keratinous fibers comprising one compartment containing the composition of claim 1, said composition containing an oxidation dye precursor and another compartment containing an oxidation agent in a cosmetically acceptable solvent.

* * * * *